(12) United States Patent
Ouchi

(10) Patent No.: US 6,506,209 B2
(45) Date of Patent: Jan. 14, 2003

(54) ENDOSCOPIC FOREIGN BODY RETRIEVING TOOL

(75) Inventor: Teruo Ouchi, Saitama (JP)

(73) Assignee: Pentax Corporation, Tokyo (JP)

( * ) Notice: Subject to any disclaimer, the term of this patent is extended or adjusted under 35 U.S.C. 154(b) by 95 days.

(21) Appl. No.: 09/797,728

(22) Filed: Mar. 5, 2001

(65) Prior Publication Data

US 2001/0021842 A1 Sep. 13, 2001

(30) Foreign Application Priority Data

Mar. 10, 2000 (JP) .......................................... 2000-066043

(51) Int. Cl.⁷ ................................................. A61B 17/28
(52) U.S. Cl. ........................................................ 606/206
(58) Field of Search .................................. 606/205, 206, 606/207, 106; 600/104

(56) References Cited

U.S. PATENT DOCUMENTS

| | | | | |
|---|---|---|---|---|
| 1,294,284 A | * | 2/1919 | Logeman | 606/131 |
| 2,584,547 A | * | 2/1952 | Cahn | 294/99.2 |
| 4,393,872 A | * | 7/1983 | Reznik et al. | 600/565 |
| 4,467,802 A | * | 8/1984 | Maslanka | 294/100 |
| 4,655,219 A | * | 4/1987 | Petruzzi | 606/206 |
| 5,147,379 A | * | 9/1992 | Sabbaghian et al. | 606/108 |
| 5,667,525 A | * | 9/1997 | Ishibashi | 606/206 |
| 5,843,121 A | * | 12/1998 | Yoon | 606/205 |
| 5,944,728 A | * | 8/1999 | Bates | 604/264 |
| 6,102,910 A | * | 8/2000 | Boebel et al. | 606/205 |
| 6,156,055 A | * | 12/2000 | Ravenscroft | 606/127 |
| 6,206,904 B1 | | 3/2001 | Ouchi | |

* cited by examiner

Primary Examiner—Danny Worrell
(74) Attorney, Agent, or Firm—Greenblum & Bernstein, P.L.C.

(57) ABSTRACT

Each of foreign body catching arms 3 has an intermediate curved portion 3a formed midway which, upon contact with the inner peripheral surface of sheath 1, undergoes elastic deformation such that the distal end portions 3b of foreign body catching arms 3 are forced to spread wider than when they are in a free state.

7 Claims, 5 Drawing Sheets

ENDOSCOPIC FOREIGN BODY RETRIEVING TOOL

BACKGROUND OF THE INVENTION

This invention relates to an endoscopic foreign body retrieving tool that is passed through a treatment tool insertion channel in an endoscope to retrieve foreign body and the like from within body cavities.

Endoscopic foreign body retrieving tools are generally designed to retrieve foreign body and the like by grasping them with a plurality of arms that "pinch" them from the outside. However, foreign body such as an artificial tooth crown is so slippery that it cannot be held stable after being grasped by the pinching action. To deal with this problem, the present inventor previously filed a patent application on an invention of an endoscopic foreign body retrieving tool having a plurality of foreign body catching arms that would function by spreading outwardly (Unexamined Published Japanese Patent Application No. 346993/1999).

While various types of endoscopic foreign body retrieving tool are disclosed in Unexamined Published Japanese Patent Application No. 346993/1999, they are classified in two major categories, one being such that a manipulating wire is pushed forward to drive a link mechanism at the tip to spread foreign body catching arms and the other being such that elastic foreign body catching arms will spread by themselves when pushed out of a sheath. However, endoscopic foreign body retrieving tools in both categories have their own problems. In order to ensure that foreign body is securely held by the spread catch arms, the manipulating wire of the retrieval tool in the first category has to be kept pushed in by the operator and if he slackens it by the slightest degree while he is retrieving the foreign body, he may drop it. In the retrieval tool of the second category, the catch arms typically formed of elastic wires will spread by themselves and the resulting spring force is the only power that is active to hold foreign body and it is sometimes insufficient to prevent the foreign body from dropping.

SUMMARY OF THE INVENTION

An object, therefore, of the invention is to provide an endoscopic foreign body retrieving tool that is so designed that a plurality of foreign body catching arms function by spreading outward and which still features high retention performance, sustaining adequate force to retain foreign body.

This object can be attained by an endoscopic foreign body retrieving tool comprising a flexible sheath, a manipulating wire provided within the flexible sheath to be capable of moving back and forth through it along the longitudinal axis and a plurality of foreign body catching arms made of an elastic material and connected to the distal end of the manipulating wire such that they spread in a free state by their own elasticity when they are outside the sheath whereas they contract if they are drawn into the sheath, characterized in that each of the foreign body catching arms has an intermediate curved portion formed midway which, upon contact with the inner peripheral surface of the sheath, undergoes elastic deformation such that the distal end portions of the foreign body catching arms are forced to spread wider than when they are in the free state.

The intermediate curved portion may draw a smooth curve which is outwardly convex when the foreign body catching arms have spread in the free state. If desired, the part of each foreign body catching arm that is beyond the intermediate curved portion toward the distal end may be oriented parallel to the longitudinal axis of the sheath when the foreign body catching arms have spread in the free state.

The distal end portion of each foreign body catching arm may be bent outward. If desired, the foreign body catching arms may be so adapted that they are entirely drawn into the sheath up to the distal end portions by pulling the manipulating wire toward the basal end.

The present disclosure relates to the subject matter contained in Japanese patent application No. 2000-66043 (filed on Mar. 10, 2000), which is expressly incorporated herein by reference in its entirety.

DESCRIPTION OF THE PREFERRED EMBODIMENT

Figure 2:
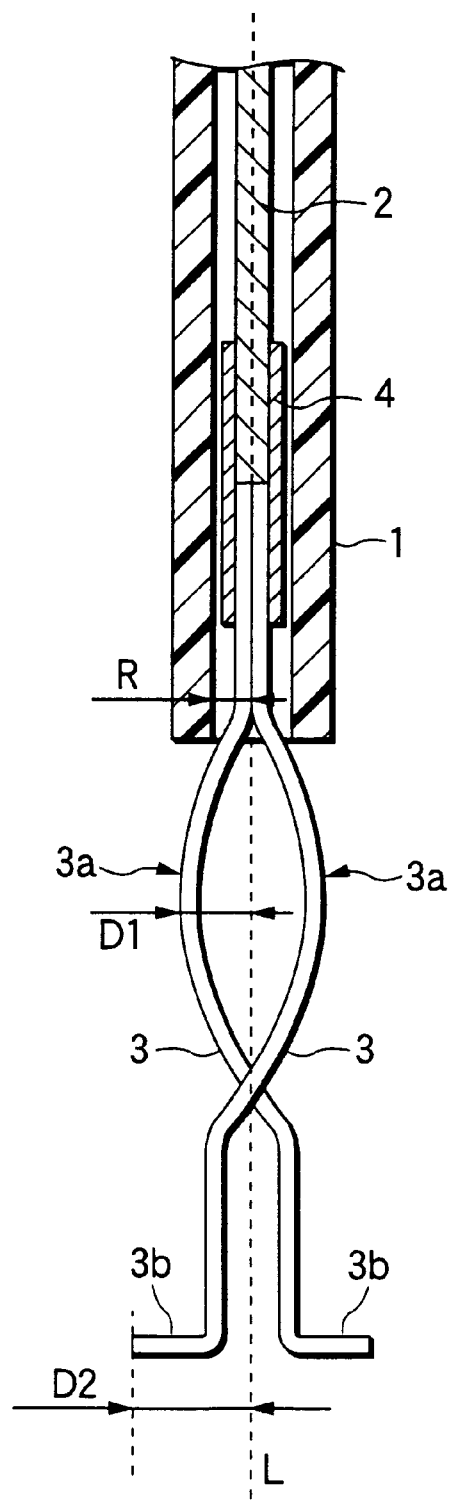
FIG. 2 is a side view showing in section the distal end portion of the same endoscopic foreign body retrieving tool for the case where the foreign body catching arms project in a free state.
Figure 3:
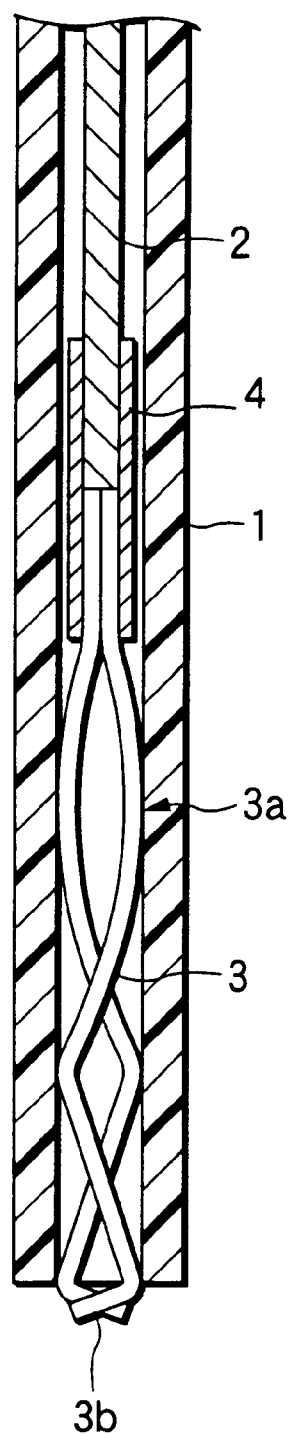
FIG. 3 is a side view showing in section the distal end portion of the same endoscopic foreign body retrieving tool for the case where the foreign body catching arms have been drawn into a sheath.

Several examples of the invention are now described with reference to the accompanying drawings. FIGS. 2 and 3 show the distal end portion of an endoscopic foreign body retrieving tool according to a first example of the invention.

The retrieval tool comprises a sheath 1 in flexible tube form that is typically made of a poly(tetrafluoroethylene) resin and which is to be inserted into or removed from a treatment tool insertion channel in an endoscope. A manipulating wire 2 is provided within the sheath 1 to be capable of moving back and forth therethrough along the longitudinal axis and it is manipulated to move back and forth by means of a manipulating section (not shown) connected to the basal end of the sheath 1.

The manipulating wire 2 has a pair of foreign body catching arms 3 connected to the distal end via a connector tube 4. The arms 3 are each made of a single wire of an elastic material such as a stainless steel wire and positioned symmetrical (180° apart) with respect to the longitudinal axis. The arms 3 may be formed of a plate or their number may be increased to three or more.

The arms 3 are each fastened to the connector tube 4 at the basal end. When they are in a free state outside the sheath 1, they spread by their own elasticity into the shape in which they were initially attached to the manipulating wire 2 (see FIG. 2). When they are drawn into the sheath 1 by means of the manipulating wire 2, the arms 3 undergo elastic deformation and contract to a smaller size (see FIG. 3).

Each of the arms 3 has an intermediate curved portion 3a formed midway which, when the arms are drawn into the sheath 1, contacts the inner peripheral surface of the sheath 1. As FIG. 2 shows, the intermediate curved portion 3a draws a smooth curve which is outwardly convex when the arms 3 have spread in the free state.

The two arms 3 cross at the distal ends of the intermediate curved portions 3a and the part of each arm that is beyond the intermediate curved portion 3a toward the arm tip is oriented parallel to the longitudinal axis of the sheath 1. The distal end portion 3b of each arm 3 is bent outward at generally right angles.

If the manipulating wire 2 is pulled toward the operator so that the arms 3 are drawn into the sheath 1 as shown in FIG. 3, the arms 3 undergo elastic deformation and contract to a size smaller than the inside diameter of the sheath 1, whereupon their distal end portions 3b move to the position where they contact the distal end face of the sheath 1.

Figure 1:
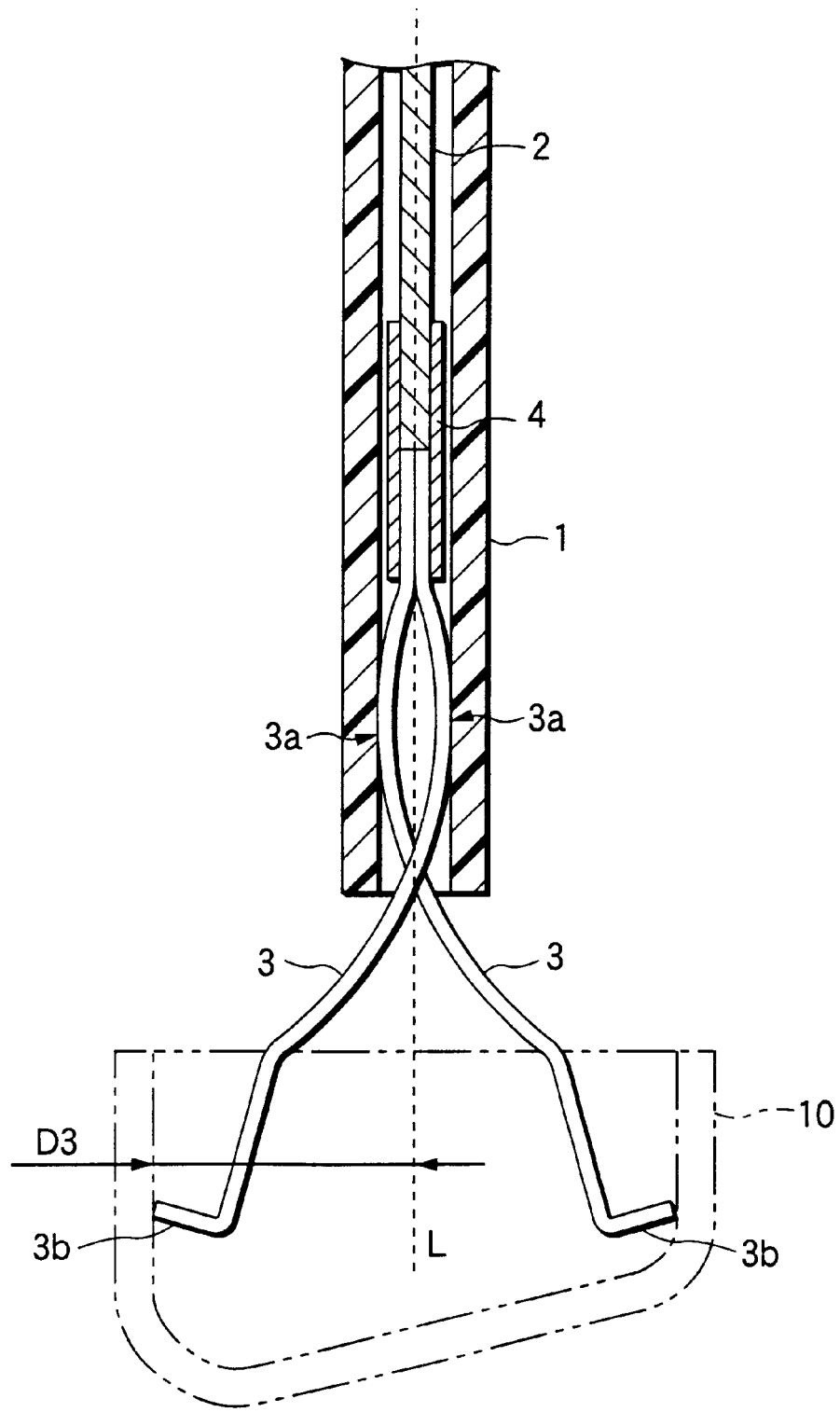
FIG. 1 is a side view showing in section the distal end portion of an endoscopic foreign body retrieving tool according to the first example of the invention as it catches foreign body.

These are the structural features of the foreign body catching arms 3 of the endoscopic foreign body retrieval tool according to the first example of the invention. When the arms 3 are drawn into the sheath 1 as shown in FIG. 1, their intermediate curved portions 3 contact the inner peripheral surface of the sheath 1 to be pushed outward, whereupon those portions 3 undergo elastic deformation and the distal end portions 3b of the arms 3 are forced to spread wider than when they are in the free state.

As a result, even a slippery foreign object such as an artificial tooth crown 10 can be held with strong force by bringing it into engagement with the arms 3 as they spread out and exert an outward force on its inner surface. The operator needs no extra step to maintain this secure state of engagement.

In the present example, each of the arms 3 has the basal end connected to the manipulating wire 2 through the connector tube 4, the distal end 3b located opposite from the basal end in a direction of the longitudinal axis L, and the intermediate curved portion 3a located between the basal end and the distal end 3b in the direction of the longitudinal axis L. As shown in FIG. 2, when the intermediate curved portion 3a is exposed from the flexible sheath 1, a maximum distance D1 between the intermediate curved portion 3a and the longitudinal axis L is larger than the inner radius R of the flexible sheath 1. Further, the intermediate curved portion 3a is located diametrically opposite from the distal end portion 3b with respect to the longitudinal axis L when the intermediate curved portion is exposed from the flexible sheath. As shown in FIGS. 1 and 2, a maximum distance D3 between the distal end 3b of the arm 3 and the longitudinal axis L when the intermediate curved portion 3a is partially retracted into the flexible sheath 1 is larger than a maximum distance D2 between the distal end 3b of the arm 3 and the longitudinal axis L when the intermediate curved portion 3a is exposed from the flexible sheath 1.

Figure 4:
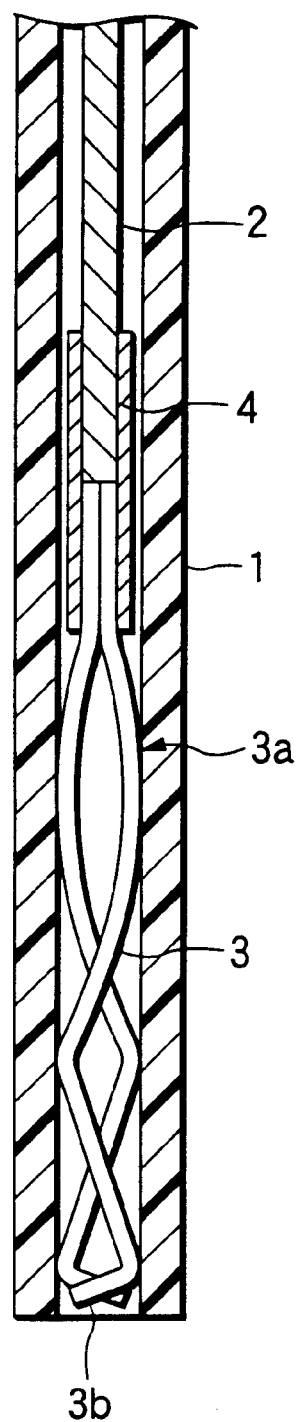
FIG. 4 is a side view showing in section the distal end portion of an endoscopic foreign body retrieving tool according to the second example of the invention for the case where the foreign body catching arms have been drawn into the sheath.
Figure 5:
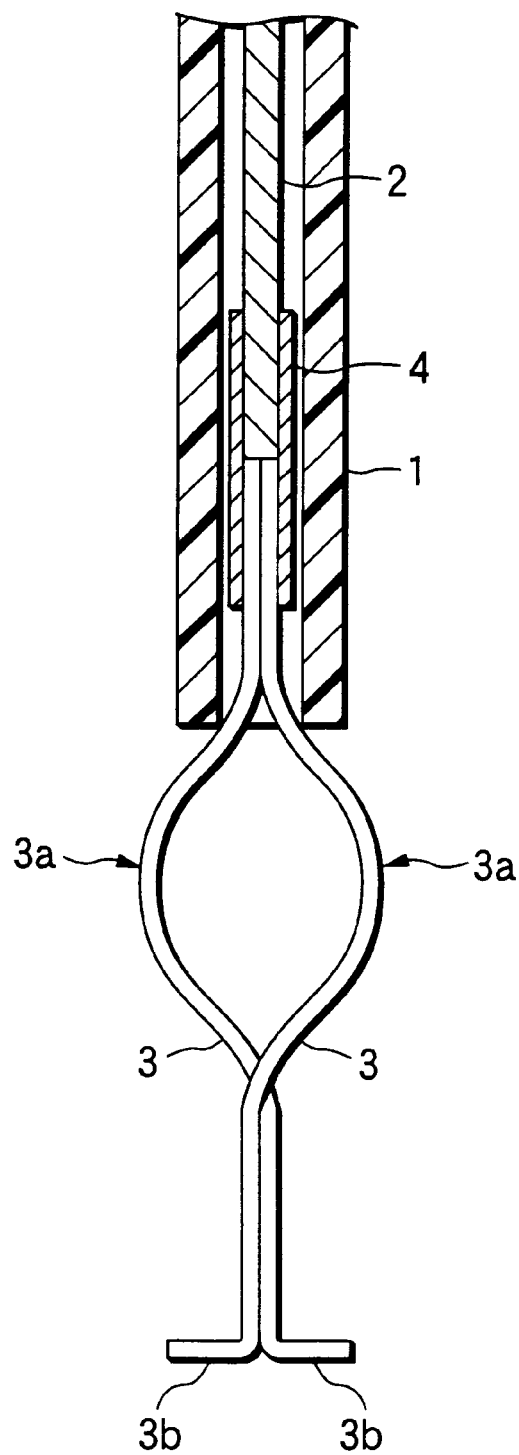
FIG. 5 is a side view showing in section the distal end portion of an endoscopic foreign body retrieving tool according to the third example of the invention for the case where the foreign body catching arms project in a free state.

The present invention is by no means limited to the example described above. If desired, the distal end portions 3b of the arms 3 may be rendered sufficiently short that the arms 3 are entirely drawn into the sheath as shown in FIG. 4. Alternatively, the intermediate curved portion 3a of each arm 3 may be rendered large (or short) enough that the arms 3 lie side by side in mutual contact in their front half as shown in FIG. 5.

According to the invention, the intermediate curved portion of each foreign body catching arm which is formed midway undergoes elastic deformation upon contact with the inner peripheral surface of the sheath and the distal end portions of the arms are forced to spread wider than when they are in the free state. As a result, an adequate force to retain foreign body can be sustained in the direction in which the arms spread and there is no dropping of the foreign body in the process of its retrieval.

What is claimed is:

1. An endoscopic foreign body retrieving tool comprising a flexible sheath, a manipulating wire provided within said flexible sheath to be capable of moving back and forth through the sheath along the longitudinal axis and a plurality of foreign body catching arms made of an elastic material and connected to the distal end of said manipulating wire such that they spread in a free state by their own elasticity when they are outside the sheath whereas they contract if they are pulled into the sheath, wherein each of said foreign body catching arms has an intermediate curved portion formed midway which, upon contact with the inner peripheral surface of the sheath, undergoes elastic deformation such that the distal end portions of the foreign body catching arms are forced to spread wider than when they are in the free state.

2. The endoscopic foreign body retrieving tool according to claim 1, wherein said intermediate curved portion draws a smooth curve which is outwardly convex when said foreign body catching arms have spread in the free state.

3. The endoscopic foreign body retrieving tool according to claim 2, wherein the part of each of said foreign body catching arms that is beyond said intermediate curved portion toward the distal end is oriented parallel to the longitudinal axis of said sheath when said foreign body catching arms have spread in the free state.

4. The endoscopic foreign body retrieving tool according to claim 1, wherein the distal end portion of each of said foreign body catching arms is bent outward.

5. The endoscopic foreign body retrieving tool according to claim 4, wherein said foreign body catching arms are so adapted that they are entirely drawn into said sheath up to said distal end portions by pulling said manipulating wire toward the basal end.

6. An endoscopic retrieving tool comprising:
 a flexible sheath having an inner radius with respect to a longitudinal axis;
 a manipulating wire passing through the flexible sheath and movable along the longitudinal axis relative to the flexible sheath; and
 a plurality of elastic catching arms, each having a basal end connected to the manipulating wire, a distal end opposite from the basal end, and an intermediate curved portion between the basal end and the distal end, wherein a maximum distance between the intermediate curved portion and the longitudinal axis is larger than the inner radius when the intermediate curved portion is exposed from the flexible sheath, and the intermediate curved portion is located opposite from the distal end portion with respect to the longitudinal axis when the intermediate curved portion is exposed from the flexible sheath.

7. The endoscopic retrieving tool according to claim 6, wherein a maximum distance between the distal end and the longitudinal axis when the intermediate curved portion is retracted into the flexible sheath is larger than a maximum distance between the distal end and the longitudinal axis when the intermediate curved portion is exposed from the flexible sheath.

* * * * *